United States Patent
van de Wijdeven

[11] Patent Number: 5,989,214
[45] Date of Patent: Nov. 23, 1999

[54] APPARATUS FOR INJECTING A RIGID CARRIER

[76] Inventor: Gijsbertus G. P. van de Wijdeven, Grotestraat 53, NL-5256 PA, Heesbeen, Netherlands

[21] Appl. No.: 08/817,698
[22] PCT Filed: Oct. 31, 1995
[86] PCT No.: PCT/NL95/00375
   § 371 Date: Jun. 30, 1997
   § 102(e) Date: Jun. 30, 1997
[87] PCT Pub. No.: WO96/13300
   PCT Pub. Date: May 9, 1996

[30] Foreign Application Priority Data

Oct. 31, 1994 [NL] Netherlands ............... 9401805

[51] Int. Cl.$^6$ .................................. A61M 31/00
[52] U.S. Cl. ............. 604/59; 604/57; 604/115; 604/134
[58] Field of Search ............ 604/59, 57, 73, 604/115, 116, 130, 134, 137, 131, 135

[56] References Cited

U.S. PATENT DOCUMENTS 3,815,605   6/1974   Schmidt et al. ............. 604/115
3,859,996   1/1975   Mizzy .

FOREIGN PATENT DOCUMENTS

2138152   12/1972   France .
90/05488   5/1990   WIPO .
91/15165   10/1991   WIPO .
93/23110   11/1993   WIPO .

*Primary Examiner*—Corrine McDermott
*Assistant Examiner*—Kent Gring
*Attorney, Agent, or Firm*—Banner & Witcoff, Ltd.

[57] ABSTRACT

The invention relates to an apparatus for injecting the body of humans or animals with a pharmaceutical preparation, wherein the preparation is arranged in a rigid carrier, wherein the apparatus comprises: a chamber into which the carrier can be transported; and a channel connecting onto the chamber for transporting the carrier into the body comprising fixation means for fixing the end of the channel relative to the skin of the body for injecting in order to prevent a movement of the channel in the direction perpendicularly of the axis of the barrel. According to one embodiment the fixation means are formed by chamfered protrusions formed on the part adapted for contact with the skin of the body and extending substantially in the direction of the axis of the channel.

16 Claims, 7 Drawing Sheets

APPARATUS FOR INJECTING A RIGID CARRIER

BACKGROUND OF THE INVENTION

The invention relates to an apparatus for injecting the body of humans or animals with a pharmaceutical preparation, wherein the preparation is arranged in a rigid carrier, wherein the apparatus comprises:

means for transporting the carrier into the chamber; and a channel connecting onto the chamber for transporting the carrier into the body.

Such an apparatus is known inter alia from WO-93/23110. Such an apparatus is furthermore known in another form from WO-91/12048.

In both cases of these known apparatus there is the danger of the injecting apparatus moving relative to the body during entry, at least at the place of entry of the carrier into the body, which can cause destruction of the carrier, excessive pain to the body for injecting and the danger of injection taking place at an incorrect location in the body.

SUMMARY OF THE INVENTION

The object of the present invention is to avoid the above stated problems.

This object is achieved in that the apparatus is provided with fixation means for fixing the end of the channel relative to the skin of the body for injecting.

As a result of these steps an adequate fixation takes place so that the above mentioned dangers are obviated.

According to a first embodiment the fixation means are adapted for clamping engagement on the skin.

According to a second embodiment the fixation means are formed by chamfered protrusions formed on the part adapted for contact with the skin of the body and extending substantially in the direction of the axis of the channel.

A preferred embodiment relates to an apparatus for injecting the body of humans or animals with a pharmaceutical preparation, wherein the preparation is arranged in a rigid carrier, wherein the apparatus comprises:

a chamber in which the carrier can be placed;

means for transporting the carrier into the chamber;

a barrel connecting onto the chamber; and discharging means for supplying pressurized gas to the chamber for expelling the carrier through the barrel. A spacer element is arranged which extends round the mouth of the barrel and which is adapted to direct the air flow preceding the carrier during discharging such that the air flow is guided at least partially along at least that part of the skin of the body for injecting where the carrier then enters the skin.

The danger is hereby avoided of contaminants possibly present on the skin being carried along with the carrier into the body and there causing infections or otherwise having an adverse effect. Also avoided is the danger, particularly when the carrier must be placed through a hirsute skin, of hairs also being carried in by the carrier and likewise having adverse effects.

According to another preferred embodiment the spacer element is adapted to hold the mouth of the barrel at a distance from the animal for injecting at least during discharging.

As a result of these steps the air flow preceding the carrier can escape between the barrel and the skin, whereby the required direction of the gas flow is obtained.

According to another preferred embodiment the spacer element is provided with recesses. Due to these recesses the gas flow escaping between the barrel and the skin can also pass through the spacer element without too many obstructions.

According to yet another preferred embodiment the spacer element is provided on its part adapted for conact with the animal with engaging means for preventing a movement of the spacer element in the direction perpendicularly of the axis of the barrel. This prevents so-called lateral slippage of the barrel whereby the position at which the carrier enters the body might be less reliably determined.

Other attractive preferred embodiments will be found in the remaining sub-claims.

BRIEF DESCRIPTION OF THE DRAWING

The present invention will be elucidated hereinbelow with reference to the annexed drawings, in which.

DETAILED DESCRIPTION OF THE INVENTION

Figures 1, 2, 3:
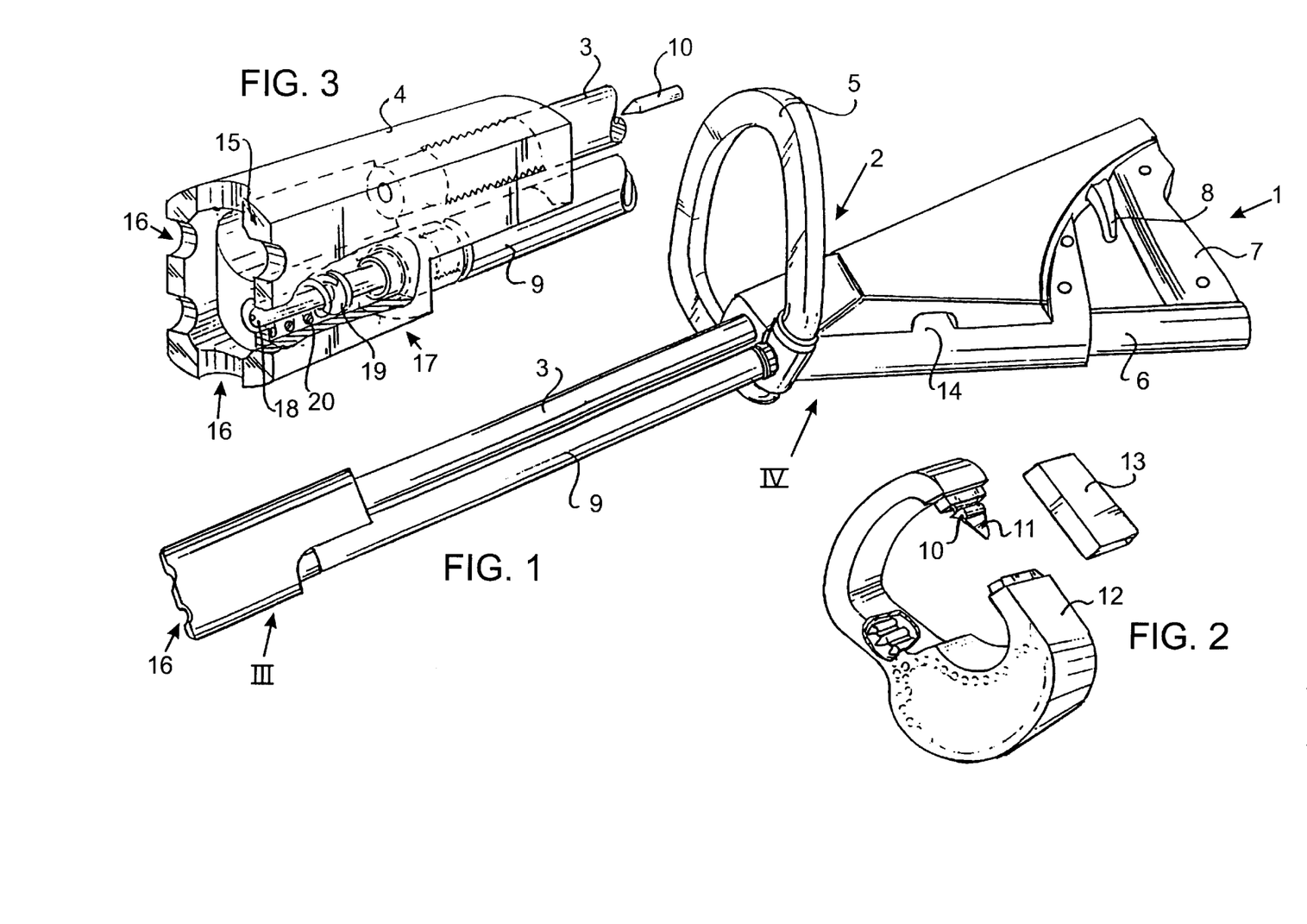
FIG. 1 shows a perspective view of an apparatus according to the invention.
FIG. 2 shows a perspective view of a holder for carriers for use with the apparatus according to the invention.
FIG. 3 shows a partly broken away perspective detail view according to arrow III in FIG. 1.

Shown in FIG. 1 is an injecting apparatus which is formed by a housing 2 to which is fixed a barrel 3, on the end of which a mouthpiece 4 is arranged. Further fixed to the housing is a bracket 5 and a pressurized gas reservoir 6 and a hand-grip 7, wherein the apparatus further comprises a trigger 8. The mouthpiece 4 and housing 2 are further connected by a connecting tube 9.

The apparatus is suitable for discharging carriers 10 which are shown in FIG. 2, wherein carriers 10 are accommodated in a belt 11. This latter is arranged in a cassette 12. The cassette has an annular construction, wherein one part is thickened for receiving the folded belt 11.

When cassette 12 is connected to the injecting apparatus 1, a removable part 13 is taken from the cassette, whereafter cassette 12 can be arranged with one end in an aperture 14 arranged for this purpose. The other end then connects onto an aoerture (not shown in FIG. 1) arranged on the upper part of the injecting apparatus.

The mouthpiece 4 is shown in more detail in FIG. 3. Mouthpiece 4 is fastened onto the barrel 3 by means of a screw connection. It should be noted here that the actual barrel, i.e. the guide for the carriers 10, is situated inside the external barrel 3 depicted in FIGS. 1 and 3.

When mouthpiece 4 is pressed against the body for injecting the mouthpiece 4 can move in axial direction relative to the actual barrel, not shown in FIG. 3, wherein mouthpiece 4 can be moved rearward relative to the relevant barrel and the discharging mechanism is set into operation.

For discharge of the air pushed out in front of the carrier 10 the edge 15 of the mouthpiece is provided with air discharge openings 16. These of course also provide for discharge of the propellant gas following the carrier 10.

Further arranged in mouthpiece 4 is an atomizing device 17 which is formed by a nozzle 18 which is connected to a reservoir (not shown in the drawing) received in the connecting tube 9. For operation thereof use is again made of the relative movement of the mouthpiece when it is pressed against a body for injecting, respectively is removed therefrom. For this purpose the nozzle 18 is provided with a concentric ring 19 and a spring 20.

It is thus possible to atomize the liquid present in the reservoir when mouthpiece 4 is pressed against the body for injecting, but equally to cause atomizing to take place when the mouthpiece 4 is moved away from the body.

The nozzle 18 is formed such that for instance a star-shaped marking is applied to the skin. It is of course likewise possible for other figures to be formed, for instance circles, squares, triangles etc. It is also possible to adapt the form of the marking by means of the edge 15 with the recess 16 or another body for placing between the skin and the nozzle.

Figure 4:
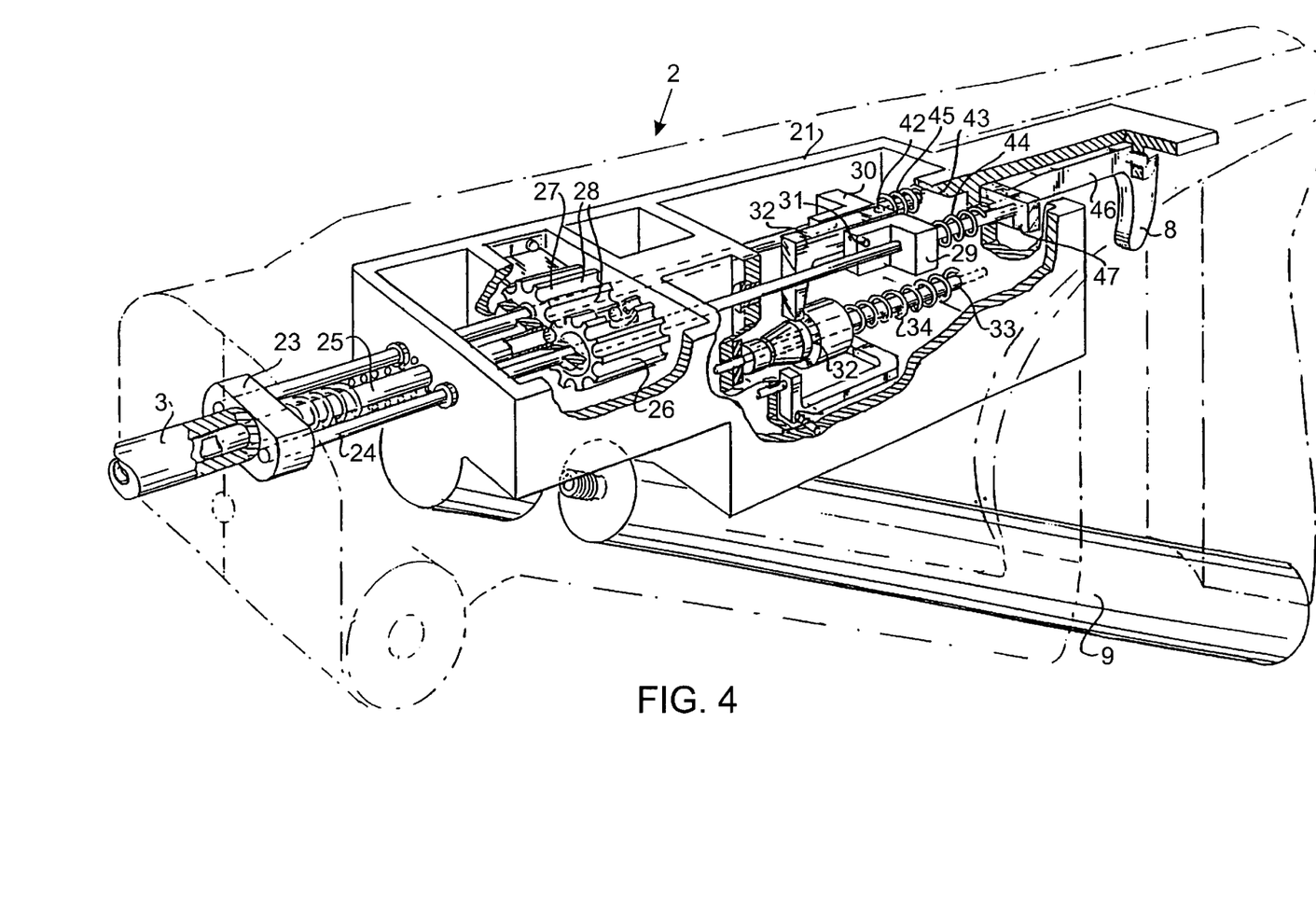
FIG. 4 shows a partly broken away perspective detail view according to arrow IV in FIG. 1.

The construction of the discharging and safety mechanism will now be elucidated with reference to FIG. 4. In housing 2 is arranged a frame 21 made of metal in which the relevant components are mounted.

The internal barrel 22 through which the carriers are fired is fixedly connected to frame 21. The external barrel 3 shown in the foregoing figures, which is axially movable relative to the barrel 22, is connected to a bridge 23 which is connected to two rods 24,25 which extend through frame 21 and which are guided through the transverse walls forming part of frame 21. It is possible to make use of other connecting elements instead of a concentric barrel. When the external barrel 3 is moved in axial direction the rods 24,25 move therewith. Two rollers 26,27 are mounted on the rods 24,25. Made in the rollers are grooves 28 which have a substantially semi-cylindrical cross section, wherein the rollers are placed relative to each other such that they are almost mutually impinging and both semi-cylindrical grooves 28 together form a cylindrical opening which forms the chamber of the discharging device.

Figure 5:
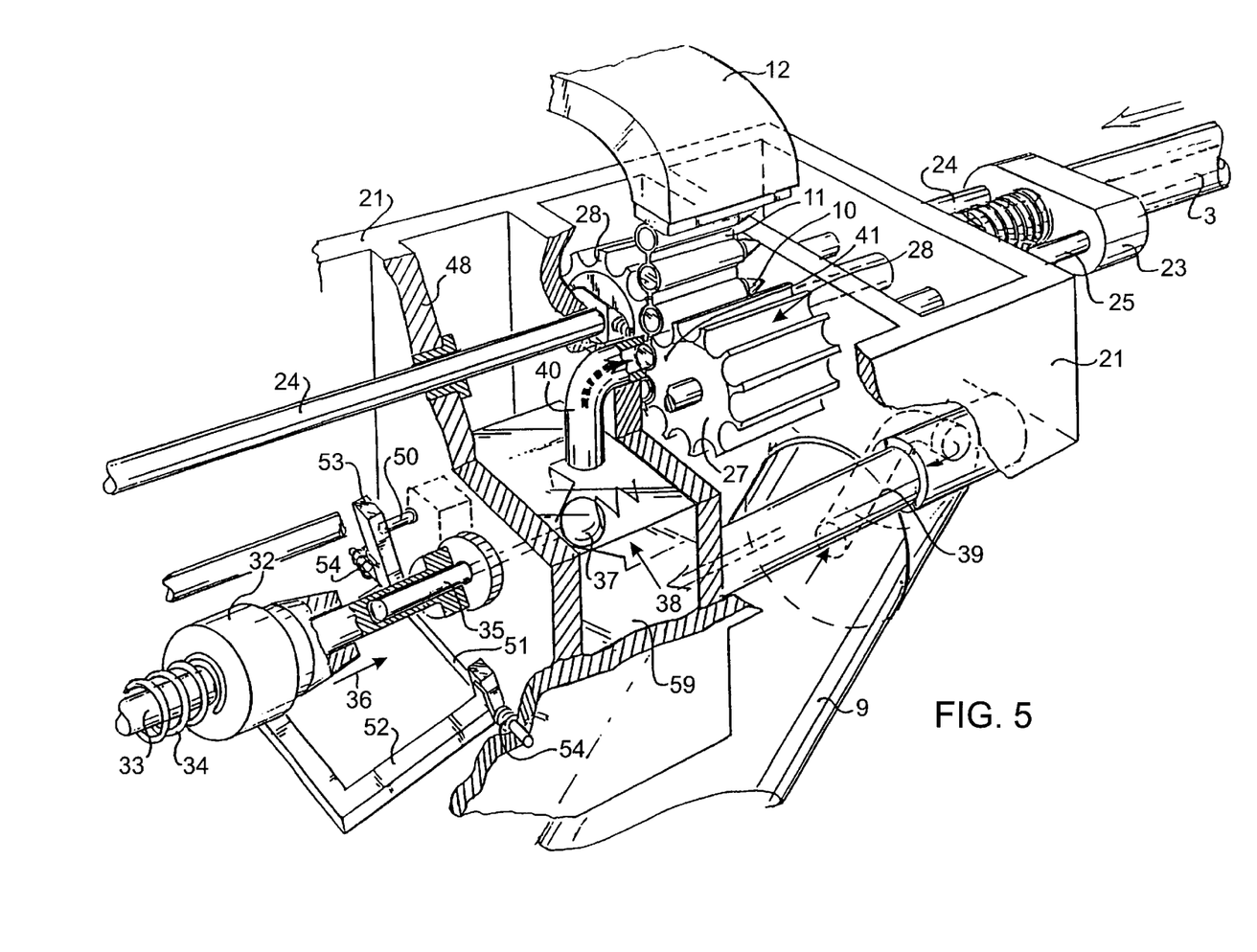
FIG. 5 shows a partly broken away perspective detail view of the part shown in FIG. 4 from the other side.

FIG. 5 shows the same device, but from the other side. The rods 24,25 are each connected to an L-shaped body 29 respectively 30 which are mutually joined by means of a shaft 31. Mounted on shaft 31 is a hook 32 which, when the rods are moved rearward in FIG. 4, is also carried along rearward by means of the angle pieces 29,30 and the shaft 31.

The hook 32 engages on a shoulder of a torpedo-shaped body 32 which is mounted on a shaft 33 extending parallel to the rods 24,25. By means of a helical spring 34 wound round shaft 33 the torpedo-shaped body 32 is urged forward. Arranged inside shaft 33 is a thrust shaft 35 which, when the torpedo-shaped body 32 moves forward in the direction of arrow 36, strikes thrust shaft 35.

Thrust shaft 35 is in turn adapted to lift the ball 37 of a ball valve 38. The latter is arranged between a pressurized air line 39 connected to reservoir 9 and a pressurized air line 40 which leads to the chamber 41 formed by two semi-cylindrical openings 28. When the barrel 3 is thus moved rearward when the mouthpiece 4 makes contact with a body for injecting, the bridge 23, the rods 24,25, the L-shaped bodies 29,30, the shaft 31, the hook 32 and therewith the torpedo-shaped body 32 are thereby moved rearward as far as a stop which is formed by the rear wall of frame 21.

Arranged on the top part of hook 22 is a ball 42 which, as it approaches the stop, rises against an inclining wall 43, whereby the hook is raised and the torpedo-shaped body 32 shoots forward as a result of the spring pressure generated by spring 34, strikes the thrust shaft 35 and the valve 37 is lifted counter to the spring force of the spring 42 arranged therein.

A determined quantity of pressurized air from the pressurized gas cylinder 9 is thus fed to the chamber 41, whereby the carrier 10 is expelled through the internal barrel 22. As a result of the action of helical springs 45,46 arranged on rods 24,25, the rods and the barrel spring are then urged back to their original position. It will thus be apparent that by pressing the mouthpiece against a body for injecting, a carrier present in chamber 41 is injected.

Figure 6:
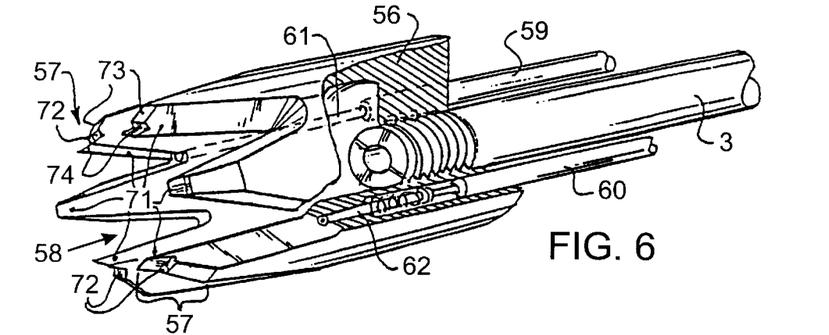
FIG. 6 is a partly broken away perspective detail view of a variant of the mouthpiece shown in FIG. 3.

When the apparatus is moved away from the body for injecting, transport of the belt 11 takes place by means of a worm wheel and freewheel mechanism (not shown) by operating the roller 27. It is of course also possible to have this take place during the movement in the reverse direction.

A number of the safety mechanisms forming part of the safety system will now be elucidated.

A first safety mechanism is formed by the trigger 8 which is connected to the lever 9. When trigger 8 is not actuated and the lever 9 is situated in the position shown in FIG. 4, the rearward movement of rods 24,25 and the components connected thereto is blocked by a connecting block 47 which is connected to both rods and the rearward movement of which is prevented by the lever 46. Only when the trigger 8 is actuated can the bridge 47 move to the rear and a carrier 10 be discharged.

A further safety mechanism is formed by a pressure measuring element. As shown most clearly in FIG. 5, on the right-hand side of the wall 48 forming part of frame 41, i.e. in the space 49 arranged there, prevails the pressure of the pressurized gas present in the pressurized gas cylinder 9. This pressure presses outward a pin 50 arranged in the relevant wall 48.

On the relevant side of wall 48 is mounted a shaft 51 on which a U-shaped lever 52 is fixed. The U-shaped lever comprises an L-shaped lever 53 which is pressed against the wall 48 by means of springs 54 arranged on shaft 51. Only when the pressure inside chamber 49, that is the pressure of the pressurized gas inside pressurized gas cylinder 9, reaches a determined value is the force exerted by the pin 50 such that it moves the U-shaped lever 52 downward counter to the spring pressure of springs 54, whereby movement of the torpedo-shaped body 32 is released. When however this pressure is too low, the U-shaped lever 52 is situated in its uppermost position whereby movement of the torpedo-shaped body 32 is prevented, as is discharging of a carrier.

FIG. 6 further shows an alternative embodiment of the mouthpiece. This alternative mouthpiece 56 is constructed wholly concentrically round the barrel 22. The edge 57 of the mouthpiece is here also provided with six recesses 58 which in the present case are distributed evenly along the round edge 57.

Between each of the recesses 58 are thus created tooth-like protrusions 71. The edge 57 of each of the protrusions 71 is defined by an imaginary truncated cone, the axis of which coincides with the axis of the barrel 3. Due to the truncated cone form the contact surfaces 57 are each provided with a flat portion 72 and the inclining portion 73 which is located further to the outside and the form of which is defined by the cone. This form has the advantage that only by pressing the apparatus according to the invention against the skin of the body for injecting at a determined angle can sufficient force be built up to depress the mouthpiece 56 sufficiently far to enable discharging. This will in any case prevent the apparatus being fired when the angle at which it is pressed against the skin differs greatly from an angle of 90°; this would result in a carrier entering the body obliquely which, as already explained, is undesirable. At a larger angle the apparatus will slip on the skin due to the oblique surface portions 72.

In order to prevent slippage when the apparatus is pressed against the body at a correct angle, tooth-like protrusions 74 are arranged on the flat portions 72.

The shown form of the teeth has the further advantage that, as stated above in the preamble, it becomes possible to deflect the air flow coming from the barrel and preceding the carrier, with the useful effect that the hairs are blown aside in a ring shape from the position where the carrier enters the body, and wherein contaminants which may be present are also carried away. Furthermore, the gas flow expelling the carrier is likewise carried away without having the opportunity to enter the body, which of course is likewise less desirable.

In addition, two reservoirs 58,59 are arranged here which are each provided with a liquid and which are activated when the mouthpiece 56 is pressed against a body for injecting. It is for instance possible herein for the one reservoir 58 to contain a marking fluid, wherein the marking fluid is atomized by the atomizer 60 connected thereto to indicate that the relevant body has been injected, while the other liquid reservoir 59 can for instance contain a disinfectant liquid which can be atomized either before or after injection to disinfect the wound formed by injecting the carrier.

It is noted herein that it is possible to disinfect or to mark prior to discharging of the carrier, that is before the actual injecting operation, or to disinfect or mark after injection. It is even possible to mark before injecting and then to disinfect or vice versa. It will be apparent that diverse other possible constructions for mouthpieces are also possible.

Figure 7:
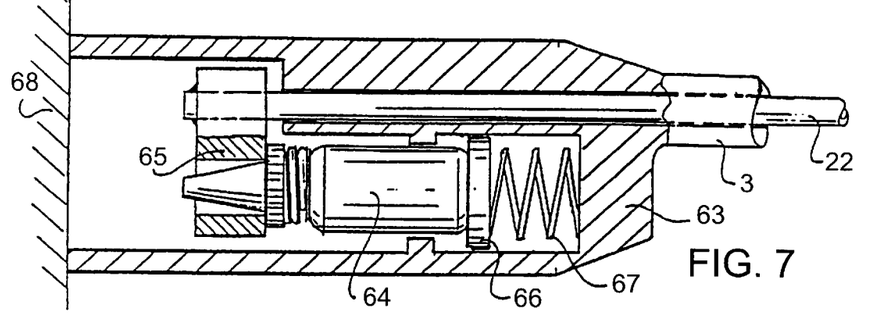
FIGS. 7–9 show sectional views of a second variant of the mouthpiece shown in FIG. 1 during different points in time of the injecting.
Figure 8:
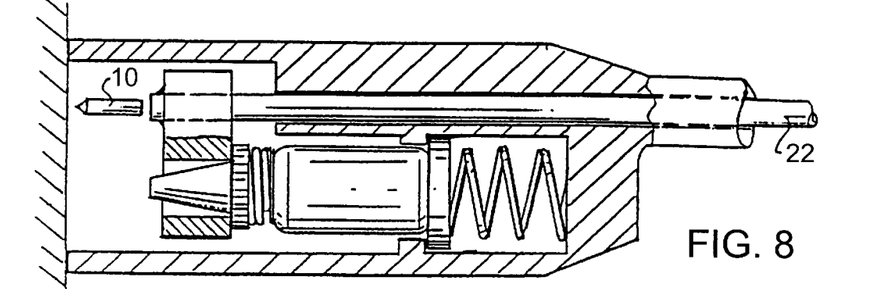
Figure 9:
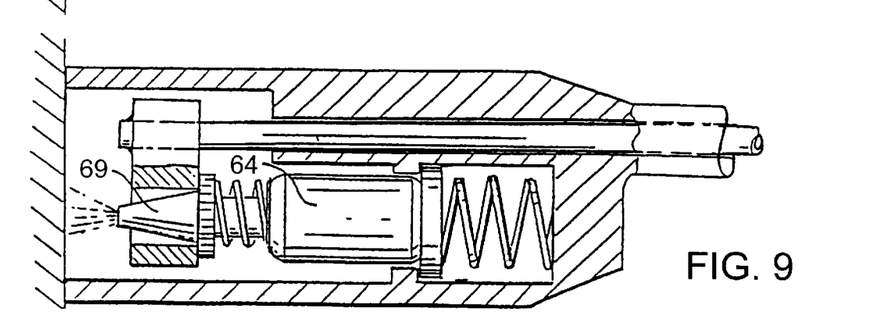

This is elucidated with reference to FIGS. 7–9 in which a second alternative embodiment of a mouthpiece is shown. This is formed by a mouthpiece 63 inside which is received a reservoir 64 for liquid for atomizing which is connected to the internal barrel 22 by means of a bracket 65 and which can be. operated by means of a thrust disc 66 and a helical spring 67.

FIG. 7 shows the rest position, wherein FIG. 8 shows how by pressing the mouthpiece 63 against a body 68 discharging of a carrier 10 is initiated, wherein in FIG. 8 is shown that carrier 10 leaves the barrel 22. With further pressing an atomizer 69 accommodated in bracket 65 is activated, which atomizes a relevant quantity of the liquid held in reservoir 64.

The design of the mouthpiece is preferably chosen such that it is possible to inject at an angle of a maximum of about 30° to the normal of the plane in which the housing of the body to be injected is located. If the angle is larger the mouthpiece slips and it is no longer possible to depress the mouthpiece so far that a carrier can be fired.

This angle of course depends on the form of the carrier, in particular the tip of the carrier. When the tip is sharp, i.e. the tip has a cone shape with a small apex angle, injection can take place at a larger angle to the normal. This is also the case when the radius of the rounding of the tip is small.

FIGS. 10–13 show schematically how carrier 10 enters the body for injecting. The mouthpiece and the barrel are only shown schematically here. The body for injecting 68 is provided with a skin 69 on which are situated hairs 70.

Figure 10:
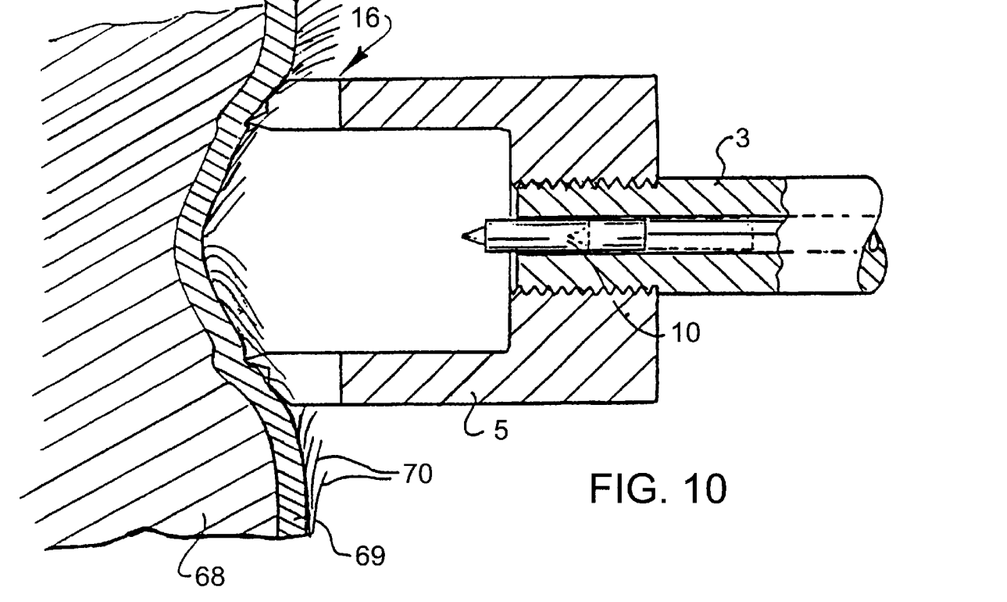
FIGS. 10–13 show sectional views of the apparatus according to the invention during the actual injecting operation.
Figure 11:
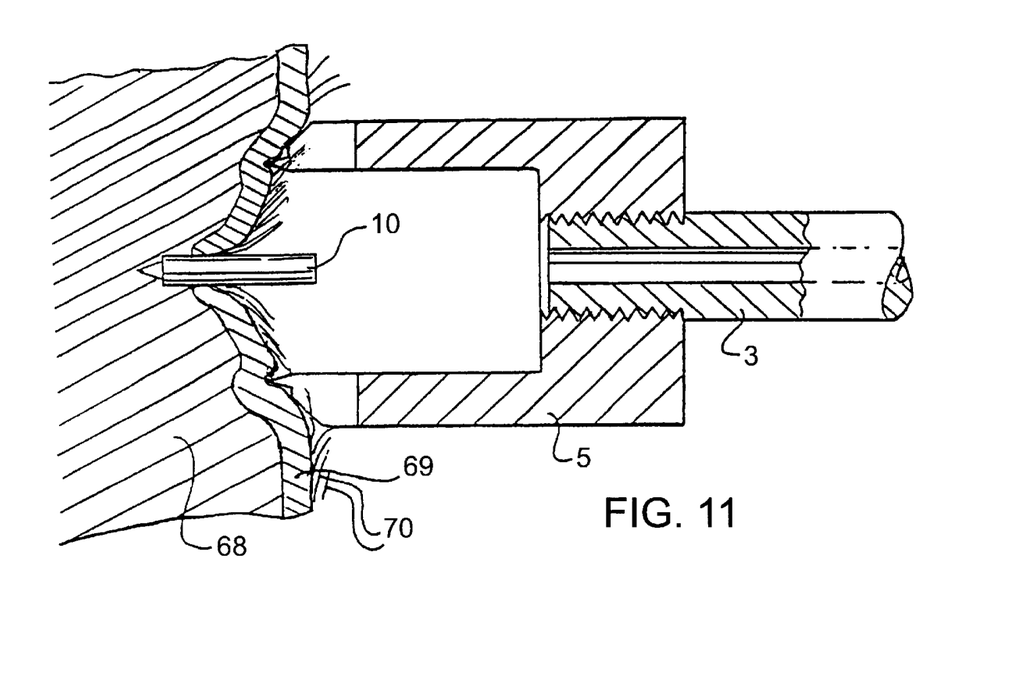

As shown in FIG. 10, the carrier 10 leaves the mouth of the barrel 3 and then cuts through the skin 69, wherein the carrier 10 enters the underlying tissue 68. The carrier 10 will continue its movement in the tissue 68 until this is damped by the density of the tissue 68 and the carrier comes to a stop.

Figure 12:
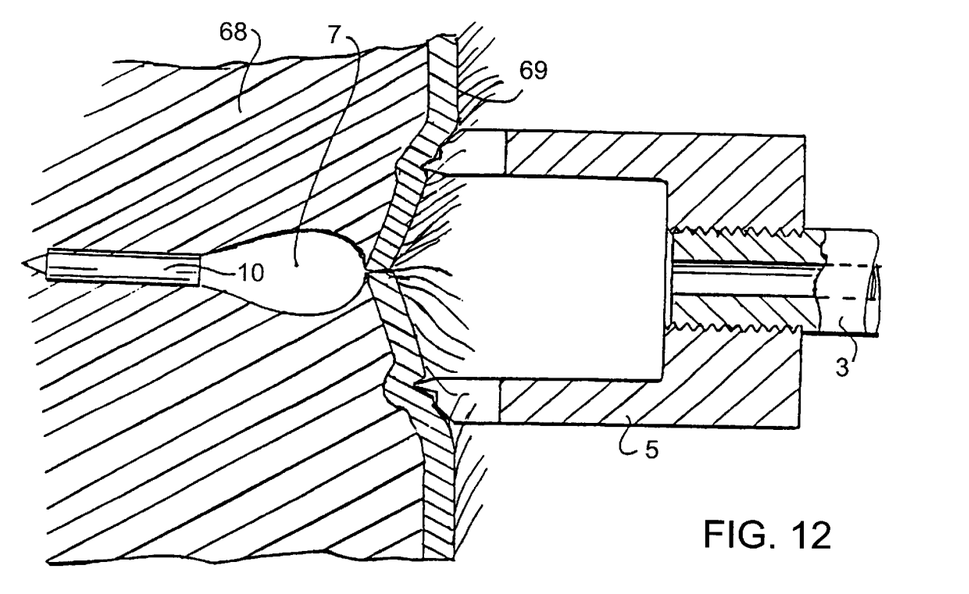
Figure 13:
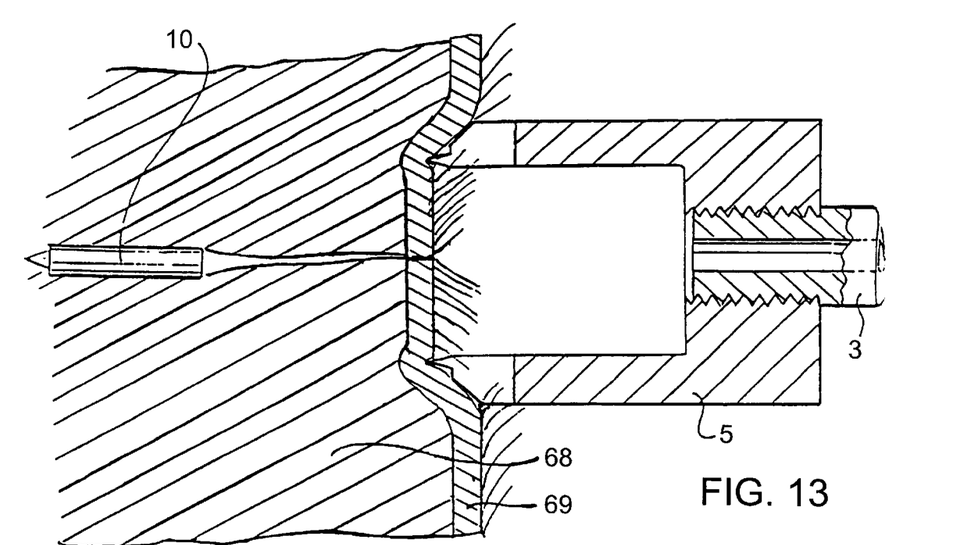

Such a situation is shown in FIG. 12. It can also be seen in this figure that as a result of the dynamic phenomena in the underlying tissue a cavity 70 forms behind carrier 10 which closes after damping of the movement phenomena, whereafter the situation shown in FIG. 13 is obtained. Here can be seen that only a very small wound results which heals easily. The carrier is subsequently broken down in the body, whereafter the pharmaceutical substance present in the carrier can perform its curative function. This is further described in the international patent application with publication number WO-93/23110.

It is pointed out that, as can be seen in FIG. 10, the air flow moving ahead of the carrier 10 blows aside the hairs 70 at the position where carrier 10 will enter the body, so that the hairs will not make entry of the carrier difficult. Blowing aside of the hairs moreover prevents the hairs being carried by the carrier into the wound, which would complicate healing of the wound. Contaminants which may be present at the relevant position are also carried away.

This provides the option of performing the disinfecting spray treatment only after entry of the carrier, which is the opposite of what is usual in the medical and veterinary arts.

Figure 14:
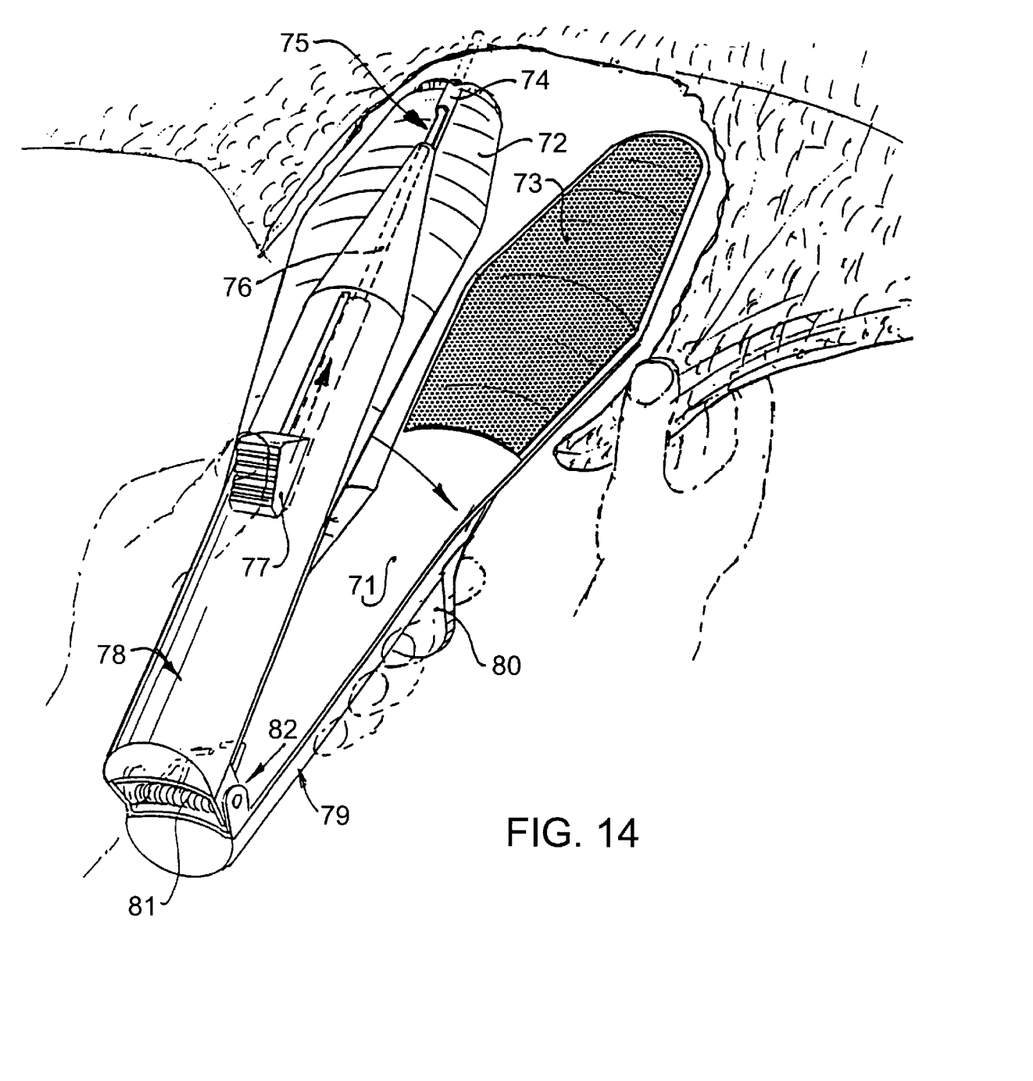
FIG. 14 is a perspective view of an alternative embodiment of the invention.

In FIG. 14 is shown an alternative embodiment of an apparatus according to the invention. This embodiment comprises two plates 71, 72 respectively which are mutually connected on their end by means of a hinge 73. Plates 71,72 are somewhat rounded at their other end and are slightly widened in the vicinity of this free end. Each of the plates 71,72 is provided on the inner side with a friction-increasing layer 73. Instead of a roughened surface it is now possible to se use of for instance ribs.

Arranged on plate 72 is a channel 74 with a substantially circular diameter. In the vicinity of the end of plate 72 and of channel 74, although still at a distance therefrom, an opening 75 is arranged in channel 74, the length of which opening is at least as great as the length of the carriers for introducing with the present apparatus.

Movable in the channel is a plunger 76 which is joined to a pressing element 77 which can be operated with the thumb. Around a part of the channel is arranged a shell 78 outside which the pressing element 77 extends.

A similar shell 79 is otherwise mounted on the other plate 71, which shell is provided with a thickening 80 to define the correct position of the fingers.

The operation of this apparatus is as follows: a fold of skin of an animal for injecting is grasped by hand, as shown in FIG. 14, wherein on each of the sides of the fold of skin is placed a plate 71, respectively 72 and the two plates are then pressed together counter to the spring pressure of spring elements 81 fixed at the hinge 73. A carrier to be injected can subsequently be placed in the opening 75 which can then be pushed inside through the skin by pressing with the thumb against the pressing element 77 by means of the plunger 76, in a manner which is otherwise per se known with a so-called trocar.

It is herein noted that by fold of skin is not only understood an actual fold of skin but also for instance a protruding soft body part, for instance an auricle. It is also important here that it is possible by means of the invention to obtain fixation of the injecting apparatus relative to the skin, which in the prior art is not possible. It will be apparent that with this "trocar" -like injecting apparatus it is also possible to use a fixation device as used in the initially described embodiment; the reverse is however equally possible; with an injecting apparatus operating with pressurized gas it is likewise possible to employ a clamping device for fixation purposes.

It will be apparent that the construction of the apparatus according to the invention can be changed in diverse ways without departing from the inventive concept. It is thus possible in the initially described embodiment to fix the container for pressurized gas to the apparatus in another manner and to assign it a dual function, for instance the additional function of handgrip. There are of course also numerous possibilities for making a construction as described with reference to FIGS. 4 and 5, particularly in respect of the safety mechanisms.

I claim:

1. Apparatus for injecting the body of humans or animals with a pharmaceutical preparation, wherein the preparation is arranged in a rigid carrier, and wherein the apparatus comprises:

a chamber in which the carrier can be transported;

a non-penetrating channel connected to the chamber for transporting the carrier into the body, and fixation means for fixing the end of the channel relative to the skin of the body for injecting in order to prevent a movement of the channel in the direction perpendicularly to the axis of the channel, said fixation means being adapted for clamping engagement to the skin.

2. Apparatus for injecting the body of humans or animals with a pharmaceutical preparation, wherein the preparation is arranged in a rigid carrier, and wherein the apparatus comprises:

a chamber to which the carrier can be transported;

a non-penetrating channel connected to the chamber for transporting the carrier into the body, and fixation means for fixing the end of the channel relative to the skin of the body for injecting in order to prevent a movement of the channel in the direction perpendicularly to the axis of the channel;

wherein the fixation means has chambered protrusions for fixing the end of the channel to the skin of the body, the chambered protrusions extending substantially in the direction of the axis of the channel, wherein the channel is formed by a barrel connecting onto the chamber; and wherein the apparatus further comprises:

discharging means for supplying pressurized gas to the chamber for expelling the carrier through the barrel; and a spacer element which extends round the mouth of the barrel and which is adapted to direct the air flow preceding the carrier during discharging such that the air flow is guided at least partially along at least that part of the skin of the body for injecting where the carrier subsequently enters the skin.

3. The apparatus as claimed in claim 2 wherein the spacer element is positioned to hold the mouth of the barrel at a distance from the body for injecting during discharging.

4. The apparatus as claimed in claim 3 wherein the spacer element has recesses.

5. The apparatus as claimed in claim 4 wherein the engaging means are adapted to allow a movement relative to the skin of the animal for injecting when the engaging means are placed at an angle relative to the normal of the skin which is greater than a predetermined angle.

6. The apparatus as claimed in claim 5 wherein the predetermined angle equals 30°.

7. The apparatus as claimed in claim 2 wherein the apparatus further comprises a safety device for only releasing the discharging means when the spacer element is arranged against a body for injecting and the spacer element is displaced relative to the barrel through a minimum distance in the axial direction of the barrel.

8. The apparatus as claimed in claim 7 wherein the engaging means are adapted to allow a movement relative to the skin of the animal for injecting when the engaging means are placed at an angle relative to the normal of the skin which is greater than a predetermined angle and the force with which the spacer element must be depressed to displace the spacer element through the minimum distance can only be generated at an angle smaller than the predetermined angle relative to the normal.

9. The apparatus as claimed in claim 7 wherein the spacer element has a side adapted for contact with the skin in the form of a truncated cone having an apex angle of 180°.

10. The apparatus as claimed in claim 9 wherein protrusions are arranged on the trancated part of the cone.

11. The apparatus as claimed in 7 including a container for pressurized gas, wherein the safety device is adapted to release the discharging means only when the pressure prevailing in the container is greater than a predetermined value.

12. The apparatus as claimed in claim 7 wherein the spacer element is connected to an atomizer.

13. The apparatus as claimed in claim 7 wherein the safety device is connected to transport means for transporting the carriers during discharging of a carrier.

14. The apparatus of claim 13 wherein the transport means comprise rollers mounted on a system of rods and having grooves wherein the form of the grooves corresponds with the form of the carrier.

15. The apparatus of claim 14 wherein the rollers are driven by a worm wheel.

16. The apparatus of claim 14 wherein the carrier is spring-mounted in the chamber in the radial direction.

* * * * *